(12) United States Patent
Voskoboynikov et al.

(10) Patent No.: US 7,314,963 B2
(45) Date of Patent: Jan. 1, 2008

(54) SPHERICAL CATALYSTS TO CONVERT HYDROCARBONS TO LIGHT OLEFINS

(75) Inventors: Timur V. Voskoboynikov, Arlington Heights, IL (US); Michael H. Quick, Arlington Heights, IL (US); Peter R. Pujado, Kildeer, IL (US); Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 8 days.

(21) Appl. No.: 10/951,359

(22) Filed: Sep. 28, 2004

(65) Prior Publication Data

US 2005/0080307 A1    Apr. 14, 2005

Related U.S. Application Data

(63) Continuation-in-part of application No. 10/106,984, filed on Mar. 26, 2002, now abandoned.

(51) Int. Cl.
*C07C 4/06* (2006.01)
(52) U.S. Cl. ...................................... 585/651; 585/653
(58) Field of Classification Search ................ 585/651, 585/653, 650
See application file for complete search history.

(56) References Cited

U.S. PATENT DOCUMENTS 3,342,750 A * 9/1967 Kearby ........................ 502/208
4,061,724 A   12/1977 Grose et al. ................. 423/335
4,104,294 A    8/1978 Grose et al. ............. 260/448 C
4,605,637 A    8/1986 Chang et al. .................. 502/64
5,171,921 A   12/1992 Gaffney et al. .............. 585/653
5,194,412 A    3/1993 Roberie et al. ................ 502/64
6,080,303 A    6/2000 Cao et al. ............... 208/120.01
6,143,941 A   11/2000 Sharma et al. ............... 585/481
6,222,087 B1   4/2001 Johnson et al. .............. 585/651
6,313,366 B1  11/2001 Ladwig et al. ............... 585/648
6,337,296 B1   1/2002 Balducci et al. ............... 502/64

FOREIGN PATENT DOCUMENTS

EP      0 109 060 A1    11/1983

* cited by examiner

*Primary Examiner*—Thuan Dinh Dang
(74) *Attorney, Agent, or Firm*—Mark Goldberg

(57) ABSTRACT

The present invention comprises a process for producing propylene comprising the steps of contacting an olefin feed containing between about 40 and about 80 wt-% olefins and between about 20 and about 60 wt-% olefins and aromatics with a spherical catalyst to form a cracked product, the catalyst comprising about 30 to about 80 wt-% of a crystalline zeolite, the reaction conditions including a temperature from about 500° to 650° C., a hydrocarbon partial pressure of 70 to 280 kPa (10 to 40 psia), a liquid hourly space velocity in the range of 5 to 40 $hr^{-1}$ and wherein propylene comprises at least 90 mol-% of the total $C_3$ products.

10 Claims, No Drawings

SPHERICAL CATALYSTS TO CONVERT HYDROCARBONS TO LIGHT OLEFINS

CROSS-REFERENCE TO RELATED APPLICATION

This application is a Continuation-In-Part of application Ser. No. 10/106,984 filed Mar. 26, 2002 now abandoned, the contents of which are hereby incorporated by reference in its entirety.

BACKGROUND OF THE INVENTION

The present invention relates to converting a hydrocarbon feed to light olefins, especially to propylene and ethylene. In particular, the present invention relates to conversion of a hydrocarbon stream containing $C_4$ to $C_8$ olefins and/or paraffins, through the use of a spherical catalyst consisting of silicalite with a non-acidic binder, to propylene and ethylene.

A low cost supply of light olefins, particularly ethylene and propylene, continues to be in demand to serve as feed for polyolefins production, particularly polyethylene and polypropylene production. Propylene is an important chemical of commerce. In general, propylene is largely derived from selected petroleum feed materials by procedures such as steam cracking, which also produce high quantities of other materials. At times, there exist shortages of propylene, which result in uncertainties in feed supplies, rapidly escalating raw material costs and similar situations, which are undesirable from a commercial standpoint.

Propylene, a light olefin consisting of three carbon atoms wherein two of the carbon atoms are joined by a double bond, has a great number of commercial applications, particularly in the manufacture of polypropylene, isopropyl alcohol, propylene oxide, cumene, synthetic glycerol, acrylonitrile and oxo alcohols.

DESCRIPTION OF THE PRIOR ART

A recently developed process for improved production of propylene is described in U.S. Pat. No. 6,222,087 B1 in which a catalyst containing ZSM-5 and/or ZSM-11, having an initial silica-to-alumina molar ratio of over 300, as well as containing phosphorus, is contacted with an olefin feed. The phosphorus is a part of the catalyst and the $C_3$ yield is described to be as much as 90% propylene or even more.

In U.S. Pat. No. 6,313,366 B1 is described a process for producing propylene from a naphtha stream comprising contacting the naphtha feed with a crystalline zeolite at the appropriate process conditions, including adding a feed of single ring aromatics to increase the propylene yield.

A spherical catalyst prepared by an oil drop method is described in U.S. Pat. No. 6,143,941. In that patent, the catalyst is used for the processing of $C_8$ aromatics to increase the concentration of a particular xylene isomer.

An object of the present invention is to provide a catalyst that converts a higher proportion of a hydrocarbon feed of $C_4$ to $C_8$ olefins to propylene and to ethylene.

A further object of the present invention is to produce a sufficiently high proportion of propylene to propane to eliminate the need for a separate propylene/propane separation step for the production of chemical grade propylene.

In still another preferred embodiment of the present invention the feed contains from about 40 to 80 wt-% olefins and from about 20 to 60 wt-% paraffins or other hydrocarbons.

SUMMARY OF THE INVENTION

The present invention comprises a process for producing propylene comprising the steps of contacting an olefin feed containing between about 40 to 80 wt-% olefins, with the majority of the rest of the feed being paraffins, with a catalyst to form a cracked product, the catalyst comprising about 30 to about 80 wt-% of a crystalline zeolite, the reaction conditions including a temperature from about 500° to 650° C., a hydrocarbon partial pressure of 70 to 280 kPa (10 to 40 psia), a liquid hourly space velocity (LHSV) in the range of 5 to 40 $hr^{-1}$, and wherein propylene comprises at least 90 mol-% of the total $C_3$ products and ethylene comprises at least 90 mol-% of the total $C_2$ products.

The cracking of the olefins is preferably carried out in a moving-bed reaction zone wherein feed and catalyst are contacted at effective olefin cracking conditions. During the reaction, a carbonaceous material—i.e. coke—is deposited on the catalyst. The carbonaceous deposit material has the effect of reducing the number of active sites on the catalyst, which thereby affects the yield. During the process, coked catalyst is withdrawn from the reaction zone and regenerated to remove at least a portion of the carbonaceous material and returned to the reaction zone. Depending upon the particular catalyst, it can be desirable to substantially remove the carbonaceous material, e.g., to less than 0.1 wt-%, or only partially regenerate the catalyst, e.g., to from about 1 to 5 wt-% carbon. Preferably, the regenerated catalyst will contain about 0 to 1 wt-% and more preferably from about 0 to 0.5 wt-% carbon.

Accordingly, in one embodiment, the present invention relates to a catalyst for converting light olefins to propylene and ethylene, comprising about 30 to 80% by weight MFI-type zeolite and about 20 to 70% by weight of a non-acidic binder selected from the group consisting of $AlPO_4$, $SiO_2$ and $ZrO_2$, and wherein said zeolite has an $Si/Al_2$ molar ratio of from about 300 to about 600.

In another embodiment, the present invention relates to a process for producing propylene comprising passing a feed stream comprising $C_4$ to $C_{10}$ olefins into a reaction zone and contacting said feed with an oil dropped spherical catalyst to form a cracked product, wherein said catalyst comprises about 30 to 80% by weight MFI-type zeolite and about 20 to 70% by weight of a non-acidic $AlPO_4$ binder.

Additional objects, embodiments and details of this invention can be obtained from the following detailed description of the invention.

DETAILED DESCRIPTION OF THE INVENTION

The present invention comprises a process for producing propylene comprising the steps of contacting an olefin feed containing between about 40 and about 80 wt-% olefins and between about 20 and about 60 wt-% paraffins with a catalyst to form a cracked product, the catalyst comprising about 30 to about 80 wt-% of a crystalline zeolite, the reaction conditions including a temperature from about 500° to 650° C., an LHSV in the range of 5 to 40 $hr^{-1}$, and wherein propylene comprises at least 90 mol-% of the total $C_3$ products. The term "liquid hourly space velocity" is defined herein as the volume of liquid feed per hour divided by the volume of the catalyst bed, where the same units are used for both volumes and the liquid volume of the feed defined in accordance with standard conditions.

The reactor section employed in the present invention is of the type usually associated with catalyst-regeneration options known to those of ordinary skill in the art, such as: (1) a semi-regenerative unit containing fixed-bed reactors maintains operating severity by increasing temperature, eventually shutting the unit down for catalyst regeneration and reactivation; (2) a swing-reactor unit, in which individual fixed-bed reactors are serially isolated by manifolding arrangements as the catalyst become deactivated and the catalyst in the isolated reactor is regenerated and reactivated while the other reactors remain on-stream; (3) continuous regeneration of catalyst withdrawn from a moving-bed reactor, with reactivation and substitution of the reactivated catalyst, permitting higher operating severity by maintaining high catalyst activity through regeneration cycles of a few days; (4) a hybrid system with semi-regenerative and continuous-regeneration provisions in the same unit or (5) a fluidized bed reactor. The preferred embodiment of the present invention utilizes continuous regeneration of catalyst withdrawn from a moving-bed reactor. A constant amount of catalyst is removed from the bottom of the catalyst bed in the reactor to another reaction chamber for regeneration while simultaneously adding the regenerated catalyst to the top of each catalyst bed.

Process conditions that are employed include temperatures from about 500° to about 650° C., preferably from about 540° to 600° C., hydrocarbon partial pressures from about 70 to 280 kPa (10 to 40 psia), preferably from about 140 to 245 kPa (20 to 35 psia) and an LHSV in the range of 5 to 40 hr$^{-1}$, preferably in the range of 10 to 20 hr$^{-1}$. Unlike some prior art processes, steam is not introduced with the olefin stream into the reaction. It is preferred that the feed residence time in the reaction zone be less than about 5 seconds, for example from about 1 to 2 seconds. These conditions will be such that at least about 60 wt-% of the $C_5^+$ olefins in the stream are converted to $C_4^-$ products, and that propylene comprises at least about 90 mol-%, preferably greater than about 95 mol-% of the total $C_3$ reaction products with the weight ratio of propylene/total $C_2^-$ products greater than about 3.5.

The preferred catalyst used in the present invention consists of about 30 to 80% by weight of a high silica MFI-type zeolite, also known as silicalite, with a molar $Si/Al_2$ ratio of about 300 to 600, preferably between about 400 and 500, and 20 to 70% by weight of a non-acidic binder comprising amorphous aluminum phosphate, formed by sol-gel methods and having a 1:1 atomic ratio of Al/P. Silicalite is a hydrophobic crystalline silica molecular sieve. Silicalite is disclosed and claimed in U.S. Pat. No. 4,061,724 and U.S. Pat. No. 4,104,294 to Grose et al, incorporated herein by reference. Silicalite differs from other zeolites in that silicalite does not exhibit appreciable ion exchange properties as $AlO_4$ tetrahedra do not comprise a portion of the crystalline silica framework.

The binder serves the purpose of maintaining the shape of the catalyst particles. The binder may be incorporated with the zeolite in any acceptable manner known to those skilled in the art. Examples of such incorporation techniques include sol-gel oil-dropping, pillings, nodulizing, marumerization, spray drying, extrusion, or any combination of these techniques.

The preferred shape of the catalyst is spherical particles, which are preferably formed by the sol-gel oil dropping methods as described below. Spherical particles have good resistance to attrition and are well suited to a moving-bed type reactor with continuous regeneration of catalyst withdrawn from the reactor. In hydrocarbon reactions, the catalysts gradually deactivate due to coke formation on the catalyst. A spherical shaped catalyst can be readily moved from the reactor through a regeneration section and back to the moving bed, allowing for both continuous reaction and continuous regeneration of the catalyst.

The silicalite zeolite used in the catalyst may be calcined, acid-washed, ion-exchanged or steamed prior to being combined with the binder and formed into the spherical catalyst shape. Such modifications may be made as known to one skilled in the art.

A non-acidic binder is used, such as $AlPO_4$, $SiO_2$ or $ZrO_2$. The preferred binder is $AlPO_4$ with a stoichiometric ratio of Al/P. This formulation results in a binder with essentially no acidity and thereby avoids potential undesirable reactions that could lower selectivity, stability and product purity. In the preferred embodiments of the present invention, it is formed from water-soluble Al and P compounds. The phosphorus may be incorporated with the alumina in any acceptable manner known to those skilled in the art. Examples of such incorporation techniques include pillings, nodulizing, marumerization, spray drying, extrusion, or any combination of these techniques. One preferred method of preparing this phosphorus-containing alumina is the gelation of a hydrosol precursor in accordance with the well-known oil drop method. A phosphorus compound is added to an alumina hydrosol to form a phosphorus-containing alumina hydrosol. Representative phosphorus-containing compounds which may be utilized in the present invention include: $H_3PO_4$, $H_3PO_2$, $H_3PO_3$, $(NH_4)H_2PO_4$, $(NH_4)_2HPO_4$, $K_3PO_4$, $K_2HPO_4$, $KH_2PO_4$, $Na_3PO_4$, $Na_2HPO_4$, $NaH_2PO_4$, $PX_3$, $RPX_2$, $R_2PX$, $R_3P$, $X_3PO$, $(XO)_3PO$, $(XO)_3P$, $R_3PO$, $R_3PS$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$ and $(RO)_2POP(OR)_2$, where R is an alkyl or aryl, such as a phenyl radical, and X is hydrogen or a halide. These compounds include primary, $RPH_2$, secondary, $R_2PH$ and tertiary, $R_3P$ phosphines such as butyl phosphine, and tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkyl-phosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof, such as the monopropyl ester, alkyl dialkylphosphinites, $(RO)PR_2$ and dialkyl alkylphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite, and pyrophosphites such as tetraethylpyrophosphate. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkylphosphorodichloridites, $(RO)PCl_2$, dialkylphosphorochloridites, $(RO)_2PCl$, dialkylphosphinochloridites, $R_2PCl$, alkyl alkylphosphonochloridates, $(RO)(R)P(O)Cl$, dialkylphosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2(S)Cl$.

Unlike prior art compositions, preferable results are found when the phosphorus-to-aluminum ratio is about 1:1.

The alumina hydrosol is typically prepared by digesting aluminum in aqueous hydrochloric acid and/or aluminum chloride solution at about reflux temperature, usually from about 80° to about 105° C., and reducing the chloride compound concentration of the resulting aluminum chloride solution by the device of maintaining an excess of the aluminum reactant in the reaction mixture as a neutralizing agent. The alumina hydrosol is an aluminum chloride hydrosol, variously referred to as an aluminum oxychloride hydroxol, aluminum hydroxychloride hydrosol, and the like, such as is formed when utilizing aluminum metal as a neutralizing agent in conjunction with an aqueous aluminum chloride solution. In any case, the aluminum chloride is prepared to contain aluminum in from about a 0.70:1 to about 1.5:1 weight ratio with the chloride compound content thereof.

In one specific embodiment, the phosphorus compound is mixed with a gelling agent before admixing with the alumina hydrosol. It is preferred that said alumina hydrosol contain the active catalytic component of the first or second discrete catalyst. Commingling of the alumina hydrosol, containing said active catalytic component, with the phosphorus-gelling agent mixture is effected by any suitable means. The resultant admixture is dispersed as droplets in a suspending medium, e.g. oil, under conditions effective to transform said droplets into hydrogel particles.

The gelling agent is typically a weak base which, when mixed with the hydrosol, will cause the mixture to set to a gel within a reasonable time. In this type of operation, the hydrosol is typically coagulated by utilizing ammonia as a neutralizing or setting agent. Usually, the ammonia is furnished by an ammonia precursor, which is added to the hydrosol. The precursor is suitably hexamethylenetetramine (HMT), or urea, or mixtures thereof, although other weakly basic materials, which are substantially stable at normal temperatures, but decompose to form ammonia with increasing temperature, may be suitably employed. It has been found that equal volumes of the hydrosol and of the HMT solution to alumina sol solution are satisfactory, but it is understood that this may vary somewhat. The use of a smaller amount of HMT solution tends to result in soft spheres while, on the other hand, the use of larger volumes of base solution results in spheres, which tend to crack easily. Only a fraction of the ammonia precursor is hydrolyzed or decomposed in the relatively short period during which initial gelation occurs.

An aging process is preferably subsequently employed. During the aging process, the residual ammonia precursor retained in the spheroidal particles continues to hydrolyze and effect further polymerization of the hydrogel whereby desirable pore characteristics are established. Aging of the hydrogel is suitably accomplished over a period of from about 1 to about 24 hours, preferably in the oil suspending medium, at a temperature of from about 60° to about 150° C. or more and at a pressure to maintain the water content of the hydrogel spheres in a substantially liquid phase. The aging of the hydrogel can also be carried out in an aqueous $NH_3$ solution at about 95° C. for a period up to about 6 hours. Following the aging step, the hydrogel spheres may be washed with water containing ammonia.

The phosphorus-containing alumina component of the two discrete catalysts of the present invention may also contain minor proportions of other well-known inorganic oxides such as silica, titanium dioxide, zirconium dioxide, tin oxide, germanium oxide, chromium oxide, beryllium oxide, vanadium oxide, cesium oxide, hafnium oxide, zinc oxide, iron oxide, cobalt oxide, magnesia, boria, thoria and the like materials which can be added to the hydrosol prior to dropping.

A preferred method for producing the catalyst involves the following procedure: Silicalite powder, aluminum hydroxychloride solution (containing 12 to 14 wt-% Al) and 85 wt-% phosphoric acid are weighed out in appropriate amounts to make a formulation containing (volatile-free basis) 67% silicalite and 33% aluminum phosphate (1:1 Al/P atomic ratio) by weight. The silicalite is dispersed in water by appropriate means with stirring, milling or other means to form a concentrated slurry (about 45 wt-%). The Al sol and $H_3PO_4$ are cooled, diluted with water and mixed to form an $AlPO_4$ solution with 5 to 7 wt-% Al. The silicalite slurry and $AlPO_4$ solution are then mixed, along with a solution of a gelling agent, HMT, which releases $NH_3$ on heating. The amount of HMT added corresponds to about 100 to 150 mol-% of the Cl content of the aluminum hydroxychloride that is used. The mixture is then fed through a vibrating perforated disc or tube to form droplets, which are directed into a heated paraffin oil column, resulting in formation of rigid spherical particles of silicalite—$AlPO_4$ gel. The gelled particles are collected at the bottom of the column, aged for several hours in hot paraffin oil and then washed with a heated dilute aqueous $NH_3$ solution. The washed spheres are then dried and calcined, to form the final spherical catalyst particles. The order of mixing of most of the components is not critical. For example, an equivalent catalyst can be formed by first mixing the silicate slurry with the Al sol, mixing the $H_3PO_4$ with the HMT solution and water and then combining these to form the dropping mixture. Alternatively, the silicalite slurry, $H_3PO_4$, HMT solution and water may be combined simultaneously to form the dropping mixture. The resulting product is silicalite bound with amorphous $AlPO_4$. The amorphous aluminum phosphate has a surface area between about 100-300 $m^2/g$ and a pore volume between about 0.5 to 1.5 cc/g. Preferably the surface area is about 150 $m^2/g$ and the pore volume is about 1 cc/g.

The catalysts are contained in a fixed-bed system or a moving-bed system with associated continuous catalyst regeneration, whereby catalyst may be continuously withdrawn, regenerated and returned to the reactors. These alternatives are associated with catalyst-regeneration options known to those of ordinary skill in the art, such as: (1) a semi-regenerative unit containing fixed-bed reactors maintains operating severity by increasing temperature, eventually shutting the unit down for catalyst regeneration and reactivation; (2) a swing-reactor unit, in which individual fixed-bed reactors are serially isolated by manifolding arrangements as the catalyst become deactivated and the catalyst in the isolated reactor is regenerated and reactivated while the other reactors remain on-stream; (3) continuous regeneration of catalyst withdrawn from a moving-bed reactor, with reactivation and return to the reactors of the reactivated catalyst as described herein; or (4) a hybrid system with semi-regenerative and continuous-regeneration provisions in the same zone. The preferred embodiment of the present invention is a moving-bed reactor with a continuous catalyst regeneration section. During the regeneration process, a portion of the coked catalyst is withdrawn from the reaction zone and regenerated to remove the carbonaceous material. Depending upon the particular catalyst and conversion, it can be desirable to substantially remove the carbonaceous material, e.g. to less than 1 wt-%. Moreover, regeneration conditions can be varied depending upon catalyst used and the type of contaminant material present upon the catalyst prior to its regeneration. The details concerning the conditions for regeneration are known to those skilled in the art and need not be further disclosed herein.

Most preferably the ethylene comprises at least 90 mol-% of the $C_2$ products and the propylene comprises at least about 90 mol-% of the $C_3$ products.

EXAMPLE 1

A zeolite-water suspension is prepared by addition of the silicalite (a calcined, steamed and acid-washed silicalite, with an $Si/Al_2$ molar ratio of about 500, 139 g, volatile-free) to water (120 g) with stirring. The resulting mixture is then circulated through a bead mill for about 5 to 20 minutes. Meanwhile, a solution is prepared containing water (45 g), HMT (70 g of a 42 wt-% solution) and $H_3PO_4$ (62.5 g of 85 wt-% acid). Finally, a solution of aluminum chlorohydrate is weighed out (120 g, 12.2 wt-% Al, 13.9 wt-% Cl). All solutions are then cooled to about 5° to 15° C. With stirring, the silicalite-water suspension is added to the aluminum chlorohydrate solution and then the water/HMT/$H_3PO_4$ solution is added. The final mixture is then stirred for about 5 to 30 minutes. It is then pumped through a vibrating tube or cylinder with perforations at the outlet end to form droplets which are directed into a vertical column containing paraffin oil heated to about 90° to 100° C. As the droplets fall though the oil column, spherical gel particles form and are collected at the outlet. The gel spheres are then held in oil at about 90° to 100° C. for a period of about 1 to 20 hours. The spheres are then drained of oil, transferred into a vertical washing column and washed for about 1 to 4 hours at about 90° to 100° C. in a continuous flow of water containing about 0.01 to 0.5 wt-% $NH_3$. The washed spheres are drained, oven-dried for about 1 to 20 hours at about 90° to 100° C. and oven-calcined in air at about 500° to 650° C. for about 1 to 20 hours. The preparation yields 190 g (volatile-free) of the final spherical catalyst.

EXAMPLE 2

The preparation is carried out as in Example 1, except that the water/HMT/$H_3PO_4$ solution is added with stirring to the aluminum chlorohydrate solution to form a solution of $AlPO_4$. The water-silicalite suspension is then added and the resulting mixture is used to form the catalyst using the same procedure and conditions as in Example 1. This gives about the same yield of catalyst and the resulting catalyst shows equivalent performance to those prepared as in Example 1.

EXAMPLE 3

Catalytic tests have been performed in a fixed-bed pilot plant, briefly described below. The pilot plant consists of three main sections: feed delivery, reactor zone, and products separation and analysis section. A hydrocarbon feed from charger is directed to a pump, which pressurizes and delivers feed to a capillary; the feed rate being controlled by the capillary inlet/outlet pressure difference. The feed rate is measured by the decrease in charger weight. It is also possible to add hydrogen, nitrogen, or other appropriate gases or mixtures thereof to the main hydrocarbon feed with a desired feed/diluent ratio. After the feed pressure is being lowered to close to process conditions (about 20 psia), the feed enters a pre-heating zone which allows liquid component(s) to vaporize and it is heated to about 400° C. The preheated feed then enters a stainless steel reactor, filled with about 15 to about 50 cc of catalyst and spacers (such as quartz wool, ceramic balls, etc), located below and above catalyst bed. The reactor is also equipped with a thermowell with a moving thermocouple inside it. The reactor internal diameter is varied to maintain the catalyst bed thickness of about 12 cm, thus allowing accurate measurement of temperature profile across the bed. Reaction products are analyzed by online gas chromatograph, located close to the reactor outlet. Liquid products are condensed from a gas into a receiver, placed onto a balance and cooled to about 0° C. The volume and composition of remaining gas products are measured by a wet test meter and yet another gas chromatograph, thus allowing calculation of the molecular weight of the gas and therefore its weight. Summation of weight of liquid products with weight of gas products enables one to mass balance the plant very well, with weight recoveries being 100+/−3% most of the time. One of the advantages of the invention is that the catalyst is not air or moisture sensitive and does not require a special pre-treatment.

The following table shows the experimental results from pilot plant testing of the present invention. Ethylene comprised over 96% of the $C_2$ olefins produced and propylene comprised 92 to 96% by weight of the total $C_3$ and propylene yield comprised about 13% by weight (about 33% of all of the olefins on a weight basis).

TABLE 1

| | Catalyst | | | |
| --- | --- | --- | --- | --- |
| | 67% Steamed Silicalite/ 33% $AlPO_4$ | | 67% Unsteamed Silicalite/ 33% $AlPO_4$ | |
| | Feed | | | |
| | 40% Isobutene/60% Isobutane | | | |
| | Run Conditions | | | |
| | 575° C., 7 psig, 14 hr$^{-1}$ LHSV @ 40.0 cc of catalyst | | 575° C., 7 psig, 20 hr$^{-1}$ LHSV @ 40.0 cc of catalyst | |
| Time On-Stream, hrs | 5 | 55 | 5 | 55 |
| Isobutene Conversion, wt- % | 55.81 | 64.00 | 68.01 | 61.17 |
| Propylene Yield, wt- % of total feed | 28.27 | 34.00 | 33.28 | 31.99 |
| Propylene/(Propylene + Propane), wt- % | 95.84 | 94.30 | 92.39 | 93.68 |
| Ethylene/(Ethylene + Ethane), wt- % | 97.42 | 96.45 | 96.10 | 96.42 |
| Total Olefins Yield, wt- % | 92.07 | 94.06 | 87.86 | 91.97 |
| Product Selectivities, wt- % | | | | |
| $H_2$ | 0.21 | 0.13 | 0.27 | 0.15 |
| Methane | 1.23 | 1.20 | 2.00 | 1.23 |
| Ethane | 0.28 | 0.38 | 0.61 | 0.47 |
| Ethylene | 10.68 | 10.30 | 15.09 | 12.75 |
| Propane | 2.04 | 2.30 | 3.90 | 3.38 |
| Propylene | 50.55 | 52.56 | 48.84 | 52.20 |
| $C_5$ Olefins | 8.41 | 8.96 | 5.66 | 7.16 |
| $C_6$ Olefins | 16.14 | 17.14 | 12.56 | 14.76 |
| BTX | 2.47 | 1.80 | 8.04 | 5.21 |
| Heavies | 7.04 | 5.93 | 4.57 | 3.63 |

EXAMPLE 4

A catalyst, prepared in accordance with procedure described in Example 1, but having different silicalite to binder ratio of 60/40, was tested according to a procedure similar to that of Example 3, using $C_4$ to $C_7$ paraffins-olefins blend. Hydrocarbon feed was diluted with 5 mol % of hydrogen. The results are provided in Table 2, with data at 0 time referring to pure feed. It is clear from the experimental data, that the feed composition change did not have an impact on propylene yield, neither on its purity.

COMPARATIVE EXAMPLE 5

An extruded catalyst, prepared with silicalite, similar to one used in Examples 1-4, bound with silica, and having a silicalite to binder ratio of 80/20, was tested according to procedure described in Example 4. The results are given in Table 2.

TABLE 2

|  | Feed Analysis | Catalyst | |
|---|---|---|---|
|  |  | 60% Steamed Silicalite/ 40% AlPO$_4$ | 80% Steamed Silicalite/ 20% SiO$_2$ |
|  |  | Run Conditions 550° C., 21 psia, 16 hr$^{-1}$ LHSV @ 15.0 cc of catalyst, 5 mol-% H$_2$ co-feed | |
| Time On-Stream, hrs | 0 | 15 | 15 |
| Products Yield, wt-% |  |  |  |
| Methane | 0 | 0.1 | 0.1 |
| Ethane | 0 | 0.1 | 0.1 |
| Ethylene | 0 | 2.4 | 2.3 |
| Propane | 0.1 | 0.5 | 0.4 |
| Propylene | 0 | 12.7 | 12.8 |
| C$_4$ Olefins | 21.9 | 16.3 | 16.2 |
| C$_5$ Olefins | 11.2 | 6.0 | 4.8 |
| C$_6$ Olefins | 7.2 | 1.0 | 1.3 |
| C$_7$ Olefins | 1.1 | 0.3 | 0.6 |
| BTX | 2.0 | 2.8 | 3.0 |
| Propylene/ (Propylene + Propane), wt-% | NA | 96.1 | 96.7 |
| Ethylene/(Ethylene + Ethane), wt-% | NA | 95.5 | 95.8 |

Light olefins resulting from the preferred process may be used as feeds for processes such as oligomerization, polymerization and related processes (hereinafter "polymerization") to form macromolecules. Such light olefins may be polymerized both alone and in combination with other species, in accordance with polymerization methods known in the art. In some cases, it may be desirable to separate, concentrate, purify, upgrade, or otherwise process the light olefins prior to polymerization. Propylene and ethylene are preferred polymerization feeds. Polypropylene and polyethylene are preferred polymerization products made therefrom. Depending upon the intended end use application of the ethylene and propylene, they may be used directly in certain reactions or they may be upgraded prior to their use in the desired application.

What is claimed is:

1. A process for producing propylene and ethylene comprising passing a feed stream comprising C$_4$ to C$_{10}$ olefins into a reaction zone and contacting said feed with a spherical catalyst at temperatures from about 500° C. to about 650° C., hydrocarbon partial pressures from about 70 to about 280 kPa and LHSV from 5 to 40 Hr$^{-1}$ to form a cracked product comprising propylene and ethylene, wherein said catalyst comprises about 30 to 80% by weight MFI-type zeolite and about 20 to 70% by weight of a non-acidic binder consisting of amorphous aluminum phosphate.

2. The process of claim 1 wherein said binder is AlPO$_4$.

3. The process of claim 1 wherein said MFI-type zeolite has a molar Si/Al$_2$ ratio between about 400 and 500.

4. The process of claim 1 wherein said binder comprises a ratio of Al:P of about 1.

5. The process of claim 1 wherein propylene comprises at least 90 mol-% of total C$_3$ products in said cracked product.

6. The process of claim 1 wherein ethylene comprises at least 90 mol-% of total C$_2$ products in said cracked product.

7. The process of claim 1 wherein said reaction zone is in a moving-bed reactor.

8. The process of claim 1 wherein a portion of said catalyst is periodically removed to a regeneration section, said catalyst is then treated to remove catalyst contaminants and then said treated catalyst is returned to said reaction zone.

9. The process of claim 1 wherein said amorphous aluminum phosphate binder has a surface area between about 100-300 m$^2$/g and a pore volume between about 0.5 to 1.5 cc/g.

10. The process of claim 1 wherein said amorphous aluminum phosphate binder has a surface area of about 150 m$^2$/g and a pore volume of about 1 cc/g.

* * * * *